United States Patent
Schnitzer et al.

(10) Patent No.: US 9,839,361 B2
(45) Date of Patent: *Dec. 12, 2017

(54) OPTICAL ANALYSIS SYSTEM AND APPROACH THEREFOR

(71) Applicant: The Board of Trustees of the Leland Stanford Junior University, Stanford, CA (US)

(72) Inventors: Mark Jacob Schnitzer, Palo Alto, CA (US); Juergen Claus Jung, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 2 days.

This patent is subject to a terminal disclaimer.

(21) Appl. No.: 14/876,620

(22) Filed: Oct. 6, 2015

(65) Prior Publication Data
US 2016/0022148 A1  Jan. 28, 2016

Related U.S. Application Data

(63) Continuation of application No. 13/540,897, filed on Jul. 3, 2012, now Pat. No. 9,161,694, which is a
(Continued)

(51) Int. Cl.
*A61B 5/00* (2006.01)
*A61B 1/07* (2006.01)
(Continued)

(52) U.S. Cl.
CPC ........ *A61B 5/0084* (2013.01); *A61B 1/00009* (2013.01); *A61B 1/043* (2013.01);
(Continued)

(58) Field of Classification Search
CPC ..... A61B 5/0084; A61B 1/00009; A61B 5/04; A61B 5/0042; A61B 5/0062;
(Continued)

(56) References Cited

U.S. PATENT DOCUMENTS 4,741,326 A    5/1988  Sidall et al.
4,878,485 A   11/1989  Adair
(Continued)

FOREIGN PATENT DOCUMENTS

WO           9838907 A1     9/1998

OTHER PUBLICATIONS

Helmchen et al. "A Miniature Head-Mounted Two-Photon Microscope: High-Resolution Brain Imaging in Freely Moving Animals." Neuron, vol. 31, 903-912, Sep. 27, 2001.*
(Continued)

*Primary Examiner* — Long V Le
*Assistant Examiner* — Angela M Hoffa
(74) *Attorney, Agent, or Firm* — Crawford Maunu PLLC

(57) ABSTRACT

Imaging, testing and/or analysis of subjects are facilitated with a capillary-access approach. According to an example embodiment, a capillary is implanted into a specimen and adapted to accept an optical probe to facilitate optical access into the specimen. In some applications, the capillary is implanted for use over time, with one or more different probes being inserted into the capillary at different times, while the capillary is implanted. Certain applications involve capillary implantation over weeks, months or longer. Other applications are directed to the passage of fluid to and/or from a sample via the capillary. Still other applications are directed to the passage of electrical information between the sample and an external arrangement, via an implanted capillary.

16 Claims, 5 Drawing Sheets

Related U.S. Application Data continuation of application No. 11/334,769, filed on Jan. 18, 2006, now Pat. No. 8,346,346.

(60) Provisional application No. 60/646,858, filed on Jan. 24, 2005.

(51) Int. Cl.
  *A61B 5/04* (2006.01)
  *A61B 1/04* (2006.01)
  *A61B 1/06* (2006.01)
  *A61B 1/00* (2006.01)

(52) U.S. Cl.
  CPC .............. *A61B 1/07* (2013.01); *A61B 5/0042* (2013.01); *A61B 5/0059* (2013.01); *A61B 5/0062* (2013.01); *A61B 5/04* (2013.01); *A61B 1/00165* (2013.01); *A61B 1/04* (2013.01); *A61B 1/06* (2013.01); *A61B 2503/40* (2013.01); *A61B 2562/0242* (2013.01)

(58) Field of Classification Search
  CPC ......... A61B 5/0059; A61B 1/07; A61B 1/043; A61B 2562/0242; A61B 2503/40; A61B 1/06; A61B 1/04; A61B 1/00165
  See application file for complete search history.

(56) References Cited

U.S. PATENT DOCUMENTS

| | | |
|---|---|---|
| 5,201,318 A | 4/1993 | Rava et al. |
| 5,257,617 A | 11/1993 | Takahashi |
| 5,337,734 A | 8/1994 | Saab |
| 5,345,941 A | 9/1994 | Rava et al. |
| 5,348,687 A | 9/1994 | Beck et al. |
| 5,402,768 A | 4/1995 | Adair |
| 5,413,092 A | 5/1995 | Williams et al. |
| 5,419,323 A | 5/1995 | Kittrell et al. |
| 5,421,337 A | 6/1995 | Richards-Kortum |
| 5,421,339 A | 6/1995 | Ramanujam et al. |
| 5,562,100 A | 10/1996 | Kittrell et al. |
| 5,612,540 A | 3/1997 | Richards-Kortum |
| 5,623,932 A | 4/1997 | Ramanujam et al. |
| 5,697,373 A | 12/1997 | Richards-Kortum |
| 5,699,795 A | 12/1997 | Richards-Kortum |
| 5,704,892 A | 1/1998 | Adair |
| 5,817,015 A | 10/1998 | Adair |
| 5,830,146 A | 11/1998 | Skladnev et al. |
| 5,842,995 A | 12/1998 | Mahadevan-Jansen |
| 5,863,287 A | 1/1999 | Segawa |
| 5,902,326 A | 5/1999 | Lessar et al. |
| 5,916,171 A | 6/1999 | Mayevsky |
| 5,920,399 A | 7/1999 | Sandison et al. |
| 5,929,985 A | 7/1999 | Sandison et al. |
| 5,991,653 A | 11/1999 | Richards-Kortum |
| 6,007,208 A | 12/1999 | Dickensheets et al. |
| 6,095,982 A | 8/2000 | Richards-Kortum |
| 6,135,965 A | 10/2000 | Tumer et al. |
| 6,176,823 B1 | 1/2001 | Foley et al. |
| 6,187,289 B1 | 2/2001 | Richards-Kortum |
| 6,208,887 B1 | 3/2001 | Clarke |
| 6,219,142 B1 | 4/2001 | Kane |
| 6,241,662 B1 | 6/2001 | Richards-Kortum |
| 6,258,576 B1 | 7/2001 | Richards-Kortum |
| 6,370,422 B1 | 4/2002 | Richards-Kortum |
| 6,423,956 B1 | 7/2002 | Mandella et al. |
| 6,438,397 B1 | 8/2002 | Bosquet et al. |
| 6,459,917 B1 | 10/2002 | Gowda et al. |
| 6,483,641 B1 | 11/2002 | MacAulay |
| 6,485,413 B1 | 11/2002 | Boppart et al. |
| 6,503,196 B1 | 1/2003 | Kehr et al. |
| 6,527,753 B2 | 3/2003 | Sekine et al. |
| 6,571,118 B1 | 5/2003 | Utzinger et al. |
| 6,580,941 B2 | 6/2003 | Webb |
| 6,587,258 B1 | 7/2003 | Kane |
| 6,593,101 B2 | 7/2003 | Richards-Kortum |
| 6,639,674 B2 | 10/2003 | Sokolov et al. |
| 6,643,071 B2 | 11/2003 | Schnitzer |
| 6,697,666 B1 | 2/2004 | Richards-Kortum |
| 6,735,463 B2 | 5/2004 | Izatt et al. |
| 6,766,184 B2 | 7/2004 | Utzinger et al. |
| 6,826,422 B1 | 11/2004 | Modell et al. |
| 6,846,565 B2 | 1/2005 | Korgel et al. |
| 6,847,490 B1 | 1/2005 | Nordstrom et al. |
| 6,863,651 B2 | 3/2005 | Remijan et al. |
| 6,909,105 B1 | 6/2005 | Heintzmann et al. |
| 6,918,946 B2 | 7/2005 | Korgel et al. |
| 7,023,558 B2 | 4/2006 | Fee et al. |
| 7,023,622 B2 | 4/2006 | Liang |
| 7,081,443 B2 | 7/2006 | Koh |
| 7,091,500 B2 | 8/2006 | Schnitzer |
| 7,105,811 B2 | 9/2006 | Dantus et al. |
| 7,291,293 B2 | 11/2007 | Marks et al. |
| 7,307,774 B1 | 12/2007 | Schnitzer et al. |
| 7,309,586 B2 | 12/2007 | Koh |
| 7,309,867 B2 | 12/2007 | Costa et al. |
| 7,336,988 B2 | 2/2008 | Schnitzer et al. |
| 7,439,497 B2 | 10/2008 | Dantus et al. |
| 7,445,894 B2 | 11/2008 | Agnew et al. |
| 7,450,618 B2 | 11/2008 | Dantus et al. |
| 7,567,596 B2 | 7/2009 | Dantus et al. |
| 7,586,618 B2 | 9/2009 | Marks et al. |
| 7,609,731 B2 | 10/2009 | Dantus et al. |
| 7,670,581 B2 | 3/2010 | Korgel et al. |
| 7,691,366 B2 | 4/2010 | Koh |
| 7,722,953 B2 | 5/2010 | Krogel et al. |
| 7,772,013 B2 | 8/2010 | Robinson et al. |
| 7,776,533 B2 | 8/2010 | Agnew et al. |
| 7,787,923 B2 | 8/2010 | Alarcon et al. |
| 7,973,936 B2 | 7/2011 | Dantus |
| 8,045,161 B2 | 10/2011 | Davis et al. |
| 8,068,899 B2 | 11/2011 | Llewellyn et al. |
| 8,099,156 B1 | 1/2012 | Schnitzer et al. |
| 8,163,633 B2 | 4/2012 | Korgel et al. |
| 8,203,120 B2 | 6/2012 | Zewail |
| 8,208,504 B2 | 6/2012 | Dantus et al. |
| 8,247,769 B2 | 8/2012 | Zewail |
| 8,300,669 B2 | 10/2012 | Dantus et al. |
| 8,311,069 B2 | 11/2012 | Dantus et al. |
| 8,346,346 B1 | 1/2013 | Schnitzer et al. |
| 8,788,021 B1* | 7/2014 | Flusberg ............... A61B 5/0059 356/318 |
| 9,161,694 B2 | 10/2015 | Schnitzer et al. |
| 2002/0035317 A1 | 3/2002 | Cheng et al. |
| 2002/0065468 A1 | 5/2002 | Utzinger et al. |
| 2002/0072657 A1 | 6/2002 | Bousquet et al. |
| 2002/0080359 A1 | 6/2002 | Denk et al. |
| 2002/0087047 A1 | 7/2002 | Remijan et al. |
| 2002/0087206 A1 | 7/2002 | Hirschberg et al. |
| 2002/0110590 A1 | 8/2002 | Shaked et al. |
| 2002/0127632 A1 | 9/2002 | Richards-Kortum |
| 2002/0135752 A1 | 9/2002 | Sokolov et al. |
| 2002/0140942 A1 | 10/2002 | Fee et al. |
| 2002/0141714 A1 | 10/2002 | Reed et al. |
| 2002/0146202 A1 | 10/2002 | Reed et al. |
| 2002/0150333 A1 | 10/2002 | Reed et al. |
| 2003/0031410 A1 | 2/2003 | Schnitzer |
| 2003/0083552 A1 | 5/2003 | Remijan et al. |
| 2003/0103262 A1 | 6/2003 | Descour et al. |
| 2003/0117715 A1 | 6/2003 | Schnitzer |
| 2003/0118305 A1 | 6/2003 | Reed et al. |
| 2003/0142934 A1 | 7/2003 | Pan et al. |
| 2004/0023415 A1 | 2/2004 | Sokolov et al. |
| 2004/0064053 A1 | 4/2004 | Chang et al. |
| 2004/0101210 A1 | 5/2004 | Weinstein et al. |
| 2004/0143190 A1 | 7/2004 | Schnitzer |
| 2004/0162489 A1 | 8/2004 | Richards-Kortum |
| 2004/0260148 A1 | 12/2004 | Schnitzer |
| 2005/0080343 A1 | 4/2005 | Richards-Kortum |
| 2005/0131399 A1 | 6/2005 | Loeb et al. |
| 2005/0143664 A1 | 6/2005 | Chen et al. |
| 2005/0157981 A1 | 7/2005 | Berier et al. |
| 2005/0159646 A1 | 7/2005 | Nordstrom et al. |
| 2005/0207668 A1 | 9/2005 | Perchant et al. |

(56) References Cited

U.S. PATENT DOCUMENTS

| | | |
|---|---|---|
| 2005/0242298 A1 | 11/2005 | Genet et al. |
| 2007/0156021 A1 | 7/2007 | Morse et al. |
| 2008/0204551 A1 | 8/2008 | O'Connell et al. |
| 2008/0208297 A1 | 8/2008 | Gertner et al. |
| 2009/0054791 A1 | 2/2009 | Flusberg et al. |
| 2010/0208054 A1 | 8/2010 | Farr |
| 2012/0281218 A1 | 11/2012 | Schnitzer et al. |
| 2015/0057549 A1* | 2/2015 | Flusberg ............ A61B 5/0059 600/476 |

OTHER PUBLICATIONS

William A. Reed, et al., "Gradient-index fiber-optic microprobes for minimally invasive in vivo low-coherence interferometry," Optics Letters, vol. 27, No. 20, pp. 1794-1796 (Oct. 2002).

Juergen C. Jung and Mark J. Schnitzer, "Multiphoton Endoscopy," Optics Letters, vol. 28, No. 11, pp. 902-904 (Jun. 2003).

Thomas D. Wang et al. "Confocal fluorescence microscope with dual-axis architecture and biaxial postobjective scanning," Journal of biomedical Optics. vol. 9 No. 4:735-742 (Jul./Aug. 2004). (Abstract Only).

Juergen Jung et al. "In Vivo Mammalian Brain Imaging Using One- and Two-Photon Fluorescence Microscopy." J. Neurophysiol. 92: 3121-3133 (May 5, 2004).

Benjamin A. Flusberg et al. "In vivo brain imaging using a portable 3.9 gram two-photon fluorescence microendoscope." Optics Letter, vol. 30, No. 17, p. 2272-2274 (Sep. 1, 2005).

Benjamin A. Flusberg et al., "Fiber-optic fluorescence imaging," Nature Methods, vol. 2, No. 12, pp. 941-950, (Dec. 2005).

Karl Deisseroth et al., "Next-Generation Optical Technologies for Illuminating Genetically Targeted Brain Circuits," The Journal of Neuroscience, 26(41), pp. 10380-10386 (Oct. 2006).

Ashkan Monfared et al., "In Vivo Imaging of Mammalian Cochlear Blood Flor Using Fluorescence Microendoscopy," Otology & Neurotology 27, pp. 144-152 (2006).

Notice of Allowance dated Sep. 4, 2012 for U.S. Appl. No. 11/334,769.

Response and allowed claims dated Mar. 5, 2012 for U.S. Appl. No. 11/334,769.

Jung, et al. In vivo mammalian brain imaging using one- and two-photon fluorescence microendoscopy. J Neurophysiol. Nov. 2004;92(5):3121-33. Epub May 5, 2004.

Levene, et al. In vivo multiphoton microscopy of deep brain tissue. J Neurophysiol. Apr. 2004;91(4):1908-12. Epub Dec. 10, 2003.

Office action dated Mar. 30, 2009 for U.S. Appl. No. 11/334,769.
Office action dated Mar. 30, 2010 for U.S. Appl. No. 11/334,769.
Office action dated May 25, 2011 for U.S. Appl. No. 11/334,769.
Office action dated Sep. 17, 2009 for U.S. Appl. No. 11/334,769.
Office action dated Oct. 15, 2008 for U.S. Appl. No. 11/334,769.
Office action dated Oct. 26, 2011 for U.S. Appl. No. 11/334,769.
Notice of Allowance dated Aug. 14, 2015 for U.S. Appl. No. 13/540,897.
Office Action dated Jan. 16, 2015 for U.S. Appl. No. 13/540,897.
Office Action dated Jun. 24, 2013 for U.S. Appl. No. 13/540,897.
Office Action dated Aug. 14, 2014 for U.S. Appl. No. 13/540,897.

\* cited by examiner

OPTICAL ANALYSIS SYSTEM AND APPROACH THEREFOR

RELATED PATENT DOCUMENTS

This patent document is a continuation under 35 U.S.C. §120 of U.S. patent application Ser. No. 13/540,897 filed on Jul. 3, 2012 (U.S. Pat. No. 9,161,694) which is a continuation of U.S. patent application Ser. No. 11/334,769 filed on Jan. 18, 2006 (U.S. Pat. No. 8,346,346), which claims the benefit under 35 U.S.C. §119(e) of U.S. Provisional Patent Application No. 60/646,858, entitled "Optical Analysis Systems and Approaches" and filed on Jan. 24, 2005.

FEDERALLY-SPONSORED RESEARCH AND DEVELOPMENT

This invention was made with Government support under contract DA017895 awarded by the National Institutes of Health. The U.S. Government has certain rights in this invention.

FIELD OF THE INVENTION

The present invention relates generally to optical analysis, and more particularly to analysis approaches involving the optical analysis of subjects accessed via a capillary.

BACKGROUND

A variety of approaches to optical imaging and analysis have been used for many different applications. For example, the endoscope is a useful tool for a variety of applications such as biological research, medical diagnostics, and for image guidance in surgical procedures. Conventional endoscopes utilize a white light source to illuminate a sample and reflected light to visualize the same sample. Such conventional endoscopes are typically limited, however, to visualizing the surface of a sample or to surface inspection within a hollow tissue cavity.

Certain types of optical analysis approaches are discussed in connection with the following patent documents: U.S. Pat. Nos. 6,485,413 and 6,423,956, and U.S. Patent application Publication Number US 2003/0142934.

Many applications for which optical analysis would be beneficial are subject to a variety of limitations to such analysis. For example, space constraints in many applications limit the use of certain tools that are not generally scaleable in a manner that would facilitate such tools' use for these applications. In addition, while certain tools have been useful in applications characterized by small space constraints, these tools are often limited in their ability to achieve desirable results, or by their ability for use with certain samples such as biological samples that may include live beings. Furthermore, many optical analysis approaches are limited to the analysis of linear optics.

Some applications benefit from subcutaneous analysis, in particular with a specimen. However, invasive analysis of a specimen can be challenging, particularly when the analysis is to be made over time. For example, when a subcutaneous area of a living specimen is to be accessed multiple times, processes used to facilitate the access must be repeated. In addition, each time a specimen is accessed subcutaneously, infection and other medical complications can arise.

The above and other issues have presented challenges to optical analysis approaches and, in particular, to optical imaging in applications exhibiting relatively small space such as for endoscopic and microscopic applications.

SUMMARY OF THE INVENTION

The present invention is directed to overcoming the above-mentioned challenges and others related to the types of devices and applications discussed above and in other applications. These and other aspects of the present invention are exemplified in a number of illustrated implementations and applications, some of which are shown in the figures and characterized in the claims section that follows.

According to an example embodiment, a capillary arrangement is adapted for insertion and coupling to a specimen for optical analysis. The capillary includes a lens-type structure near a lower end thereof, which is inserted into the specimen. Walls of the capillary facilitate an opening into the specimen and to a depth at the lower end, with an opening in an upper portion of the capillary facilitating access into the capillary and into a region of the specimen optically accessible via the lower end of the capillary.

According to another example embodiment, a glass capillary having an opening at both ends thereof is attached to a polished coverslip that is affixed to one end of the glass capillary. The end of the glass capillary with the polished coverslip affixed thereto is inserted into a specimen to facilitate optical access into the specimen via the coverslip. The capillary and coverslip accept one or more of a variety of probes inserted thereto and that access the specimen via the coverslip. The arrangement of the capillary and coverslip thus allow access into the specimen (e.g., subcutaneous access) without necessarily exposing tissue in the specimen to a probe or other materials or conditions in or around the capillary.

According to another example embodiment of the present invention, an optical system facilitates accessing to and analysis of an internal portion of a sample. The system includes an optical access arrangement having an embedded end in the sample and an exposed end extending at least to an external surface of the sample. Sidewalls extend from the embedded end to the exposed end, where the sidewalls and the embedded end separate an internal portion of the sample from an external environment located at the exposed end and within the sidewalls. That is, an area within the sidewalls and bounded at the embedded end is exposed to air or other environmental conditions at the exposed end. The optical access arrangement is further adapted to accept an optical probe within its sidewalls and extending to the embedded end, such as with a probe inserted from a location at the exposed end and into the sample; the sidewalls and embedded end thus separate the probe and the external environment from an internal portion of the sample. A lens-type arrangement is at the embedded end of the optical access arrangement and facilitates the passage of light into the sample. A light director directs light, via the lens-type arrangement, to a target location in the sample and further directs light from the target location to a light detector. Such a light director may, for example, include an optical fiber, one or mirrors, or other devices or components that facilitate the passage of light. A light detector receives light from the sample, via the light director, and presents a signal characterizing the detected light.

According to another example embodiment of the present invention, an optical capillary arrangement is for implantation into subcutaneous tissue of a being. The arrangement includes a lower distal end separated from an upper distal end by sidewalls extending therebetween, and is adapted to accept an optical probe extending to a subcutaneous depth into the being. The lower distal end and sidewalls separate subcutaneous tissue of the live being from an external environment within the sidewalls upon implantation. The sidewalls include an exchange passage adapted to exchange at least one of fluid and electrical signals between a target region in the subcutaneous tissue and an environment at the upper distal end. In this context, the exchange passage may include one or more of an electrically conducting material and/or a fluid-passing tube or membrane.

According to another example embodiment of the present invention, a method for analyzing subcutaneous tissue of a live being involves inserting a lower distal end of a capillary into the subcutaneous tissue. The capillary has sidewalls extending from the lower distal end to an upper distal end, wherein the upper distal end remains exposed over a surface of the sample after insertion of the lower distal end. The subcutaneous tissue is separated from an environment in the capillary by the lower distal end and the sidewalls. An optical probe is inserted into the capillary and the subcutaneous tissue is imaged. The optical probe is removed and the live being is allowed to move freely. At a time after removing the optical probe and allowing the live being to move freely, an optical probe is re-inserted into the capillary and the subcutaneous tissue is re-imaged.

The above summary is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings in which.

Figure 1:
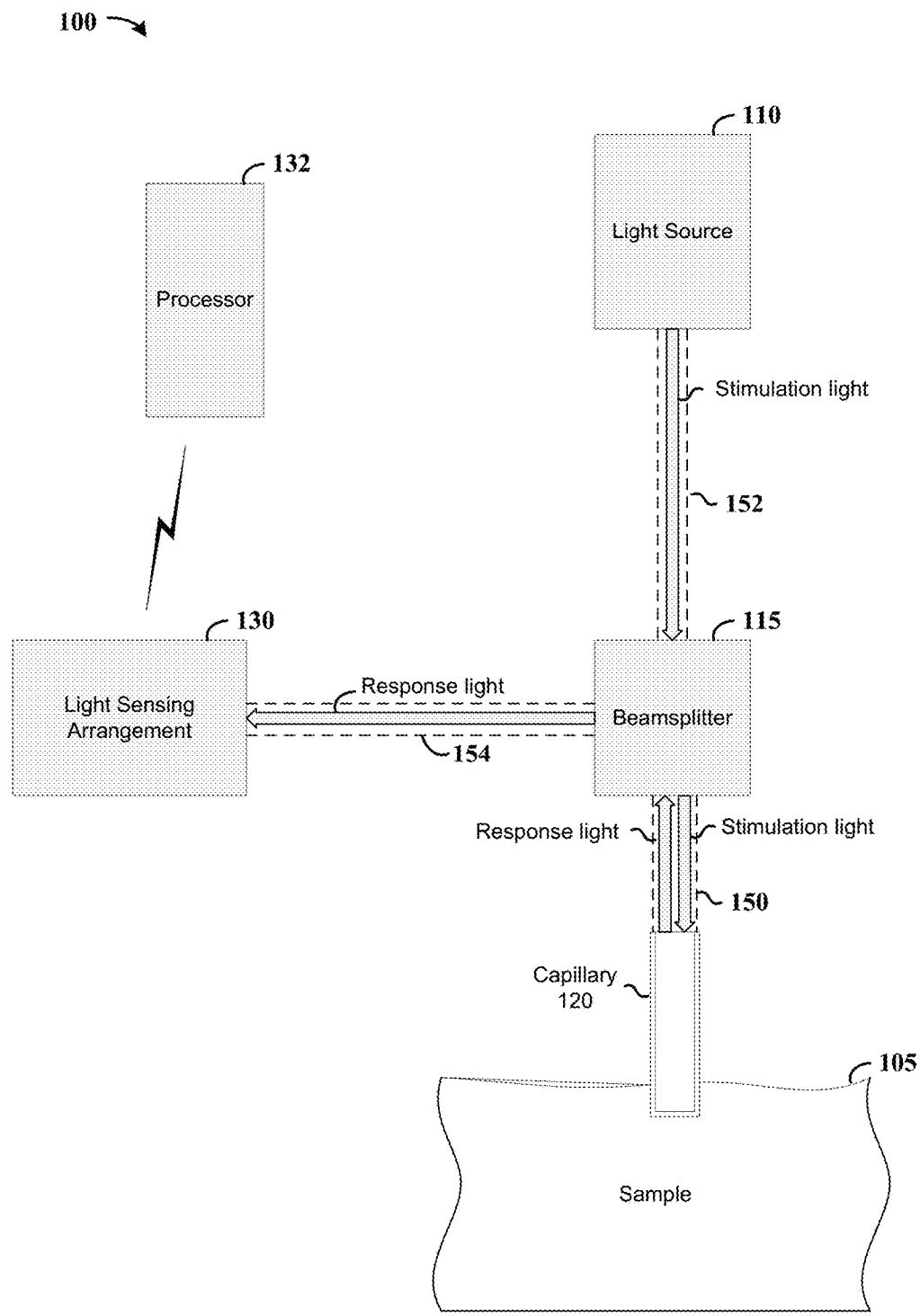
FIG. 1 shows a system for optical imaging, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices and approaches, and the invention has been found to be particularly suited for approaches to optical analysis involving the imaging of beings, and is applicable to in-vivo analysis. While the present invention is not necessarily limited to such applications, various aspects of the invention may be appreciated through a discussion of various examples using this context.

According to an example embodiment of the present invention, an optical analysis arrangement includes an implantable capillary-type device that facilitates acute (single) and/or iterative access to internal areas (e.g., tissue) of a specimen via an externally-applied probe, such as an optical probe inserted into the capillary-type device from outside the specimen. The capillary-type device is adapted to couple to a specimen, such as a living being, and to remain in an implanted state. A portion of the capillary implanted in the specimen and adjacent a target area for testing is adapted to pass light between an external probe-type arrangement and the target area in the specimen.

In another example embodiment of the present invention, an optical analysis capillary-type approach facilitates the optical analysis of a sample such as a biological specimen or a living being, for single or iterative analysis applications. A capillary is configured for accepting an optical probe, such as an endoscopic probe via an open end of the capillary, with a closed end of the capillary facilitating the passage of light between the specimen and the probe. A portion of the capillary including the closed end thereof is implanted into a sample, with the open end accessible for insertion of an optical probe.

In some instances, an optical probe implemented with one or more of the capillary-type approaches described herein is a microendoscope probe, such as those based on GRIN lenses. Various example embodiments are directed to the user of GRIN lens applications similar to those described in the following U.S. Patent Publications, each of which lists Mark Schnitzer as an inventor thereof: No. 20040260148 entitled "Multi-photon endoscopic imaging system"; No. 20040143190 entitled "Mapping neural and muscular electrical activity"; No. 20030118305 entitled "Grin fiber lenses"; No. 20030117715 entitled "Graded-index lens microscopes"; No. 20030031410 entitled "Multi-photon endoscopy"; No. 20020146202 entitled "GRIN fiber lenses"; and No. 20020141714 entitled "Grin-fiber lens based optical endoscopes"; all of which are fully incorporated herein by reference.

In other particular instances, an optical probe implemented with one or more of the capillary-type approaches described herein includes optical fibers, and in some applications, a bundle of optical fibers. Various example embodiments are directed to the use of optical fibers such as those described in the following U.S. Patent Publications: No. 20050157981 entitled "Miniaturized focusing optical head in particular for endoscope" (to Berier et al.), No. 20050207668 entitled "Method for processing an image acquired through a guide consisting of a plurality of optical fibers" (to Perchant, et al.), No. 20050242298 entitled "Method and equipment for fiber optic high-resolution, in particular confocal, fluorescence imaging" (to Genet, et al.) and No. 20030103262 entitled "Multimodal miniature microscope" (to Richards-Kortum, et al.); and as those described in the following U.S. Pat. No. 6,766,184 (Utzinger, et al.) entitled "Methods and apparatus for diagnostic multispectral digital imaging," U.S. Pat. No. 6,639,674 (Sokolov, et al.) entitled "Methods and apparatus for polarized reflectance spectroscopy," U.S. Pat. No. 6,571,118 (Utzinger et al.) entitled "Combined fluorescence and reflectance spectroscopy," and U.S. Pat. No. 5,929,985 (Sandison, et al.) entitled "Multispectral imaging probe," all of which are fully incorporated herein by reference.

In a more particular example embodiment, a capillary as discussed in the preceding examples is further adapted to facilitate the micro-fluidic delivery and sampling to and/or from a specimen. Supplied fluids may include, for example, fluids that facilitate the detection of optical characteristics of a target location in the specimen, or fluids that include drugs and/or other substances that affect the specimen. Microfluidic transfer from a specimen may involve, for example, online recovery of fluid specimens for off-line genetic, biochemical, chemical, genomic, proteomic, or cytometric analyses. In some embodiments, fluid lines are permanently implanted in a specimen along with the capillary. In other embodiments, the fluid lines are inserted into the specimen (and reinserted for subsequent analysis) via specific routes in the capillary.

In another example embodiment, a capillary as discussed in the preceding examples is further adapted to pass a stimulus into a specimen to facilitate the detection of characteristics of the specimen and, in some instances, the characteristics of a particular target area in the specimen. In one implementation, the stimulus is an electrical stimulus, passed from the capillary to a target area. One or more electrodes at an implanted portion of the capillary facilitate the passage of the electrical stimulus into the specimen. In another implementation, electrodes at an implanted portion of the capillary are used to facilitate in vivo recordings of nervous, cardiac, or muscular activity at the imaging field. In another implementation, a chemical stimulus, such as that delivered via a fluid as discussed above, is applied to the target area via the capillary. In some embodiments, electrodes are permanently implanted in the specimen along with the capillary, and in other embodiments, the electrodes are inserted into the specimen (and reinserted for subsequent analysis) via specific routes in the capillary.

In other example embodiments, the capillary includes optical devices such as lenses, filters, polarizers or other devices that facilitate the passage of light between a probe and a sample. In certain example embodiments, the capillary is implemented with a cover slip, or sheath, that facilitates implantation into a specimen. In another example embodiment, at least some of the capillary is coated or otherwise configured with material that inhibits certain adverse characteristics of invasive implantation into live beings.

In another example embodiment of the present invention, an approach to optical analysis involves the use of a micro-mirror arrangement, including one or more mirrors, integrated with a light directing capillary-type arrangement to facilitate optical stimulation and response detection with a sample. The micro-mirror arrangement is used to direct light to a sample, with light from the sample being collected and used for analyzing the sample (i.e., detecting a response, or condition, of the sample). The micro-mirror arrangement is selectively implemented in the capillary-type arrangement, facilitating near-target placement of the micro-mirror arrangement while also enabling access to the micro-mirror arrangement from an external position, without necessarily removing the capillary-type arrangement or otherwise disturbing the sample.

In some applications, the micro-mirror arrangement includes a MEMS (micro-electro-mechanical systems) mirror, and the optical analysis approach therewith involves the optical stimulation of a sample to generate nonlinear optical responses. Certain approaches are thus implemented to facilitate the detection of a nonlinear response. For example, certain stimulation approaches known to generate nonlinear optical responses are used in connection with a sample and the scanning of the sample with the MEMS mirror. Detected nonlinear optical responses to the scanning are made available for use in analyzing the sample.

In certain implementations, arrangements with which the MEMS mirror is used are configured for directing response light of a wavelength different than that of stimulation light, to facilitate the detection and analysis thereof. In one application, a light detector and/or a light director (something that directs light) is implemented to analyze wavelength-related characteristics of a response of the sample via an implanted capillary-type arrangement. For instance, where light of a particular wavelength is directed to the sample via a MEMS mirror, light of a different wavelength is collected from the sample as a response, and analyzed accordingly. Certain characteristics of a light collector (or detector) are selectively tailored to facilitate the detection of light at such a different wavelength. Some applications involve the use of a wavelength-dependent dichroic element, such as a beam splitter, that directs light of a particular wavelength (e.g., the wavelength of light related to a response of the sample) to a detector.

In another example embodiment of the present invention, a light director is adapted for analyzing a sample using a movable micro-mirror and a dichroic device to selectively pass stimulation and response light. The micro-mirror is moved using an actuator, such as a pivoting or translating actuator, for controllably moving the mirror to direct light from a light source, such as a laser or incandescent source, to different target locations on the sample. The dichroic device includes one or more wavelength-selective components, such as a beam splitting prism, a dichroic mirror or a curved dichroic beam splitter. Such a dichroic device is selectively placed in the capillary-type arrangement, where appropriate, for selective wavelength-dependent direction of light into and/or from a sample. In some applications, the dichroic device is used to separate wavelengths that are subsequently used to generate a multi-channel image.

According to another example embodiment of the present invention, an optical system is adapted for analyzing a sample. The system includes a light source, a light director, an implantable capillary-type arrangement, a dichroic device and a light detector. The light director includes a micro-mirror, an actuator and a dichroic device, and is selectively located in the capillary-type arrangement. The actuator (e.g., a MEMS motor) is adapted to controllably move the mirror, such as by pivoting the mirror about one or more axes or moving the mirror laterally and/or vertically relative to the sample. The mirror is controllably moved to direct light from the light source to different target locations on the sample. In some applications, the actuator is adapted to move the micro-mirror in a manner that causes light to scan across a target area in the sample (i.e., via an embedded lens at a lower end of a capillary-type arrangement).

The dichroic device is adapted to pass light from the light source to the sample and to direct response light from the sample to a light detector (e.g., using wavelength-dependent characteristics of the dichroic device to selectively direct the response light to the light detector). The dichroic device may be implemented using one or more of a variety of approaches, such as those involving a beam splitter or other wavelength-selective component as discussed herein.

The light detector is configured and arranged to receive light from the sample, via the capillary-type arrangement and the dichroic device, and to present a signal characterizing the detected light. The light detector is implemented using one or more of a variety of devices, such as a photo detector, light collector, photo multiplier tube, imaging electronics, lenses and others as discussed, e.g., in connection with other embodiments and implementations herein.

Turning now to the Figures, FIG. 1 shows an optical analysis system 100, according to another example embodiment of the present invention. The optical analysis system 100 includes a light source 110 and a capillary 120 arranged to facilitate the selective direction of light from the light source to a target location or locations on a sample 105 (e.g., a specimen). In some applications, the light source 110 is a laser. A variety of lasers can be used with the light source 110, with a few examples including an Argon ion laser, a YAG laser, a laser diode, a Titanium sapphire laser, a superluminescent diode and a Chromium-fosterite laser. Target locations may include, for example, locations of interest for a particular type of analysis or specific locations relating to implanted devices, such as probes, that facilitate the detection of a response from the sample.

Stimulation light from the light source 110 is directed to the capillary 120 via a beam splitter 115 (or similar device). Response light from the sample 105 (e.g., reflected and/or refracted light) is returned to a sensing arrangement 130 via the beam splitter 115. The detector 130 may, for example, include a photo-multiplier tube (PMT), a CCD camera or any arrangement that can process light to generate an output that can be used to characterize, and/or to produce an image from, the light from the sample. In some implementations, a processor 132 such as a computer or other device is used to characterize the light and/or to reconstruct a digital image in such a manner.

In some applications, mirrors are implemented in connection with FIG. 1 to direct light to the sample 105 via a lower end of the capillary 120, and include a variety of structures and implement a variety of approaches, depending upon the particular application. In one example, a MEMS mirror is implemented in connection with the capillary 120, to facilitate light direction, scanning and/or other light-related application functions.

A light conduit 150, such as a fiber optic conduit, is optionally implemented to facilitate the transport of light from the beam splitter 115 into the capillary 120 and to the target location. In some applications, the light conduit 150 is a single conduit and, in other applications, the light conduit 150 includes two or more light conduits that are selectively implemented, e.g., for passing light to and/or from the sample 105. Similar light conduits 152 and 154 are selectively implemented with the transport of light respectively from the light source 110 to the beam splitter 115, and from the beam splitter 115 to the light sensing arrangement 130.

In some particular instances, the light conduit 150 is a microendoscope probe, such as those based on GRIN lenses as described in the U.S. Patent documents listing Mark Schnitzer as an inventor and cited above. In other particular instances, the light conduit 150 is an optical probe having a bundle of optical fibers, such as those described in the U.S. Patents and Patent Publications referenced above in connection with fiber applications.

Figure 2:
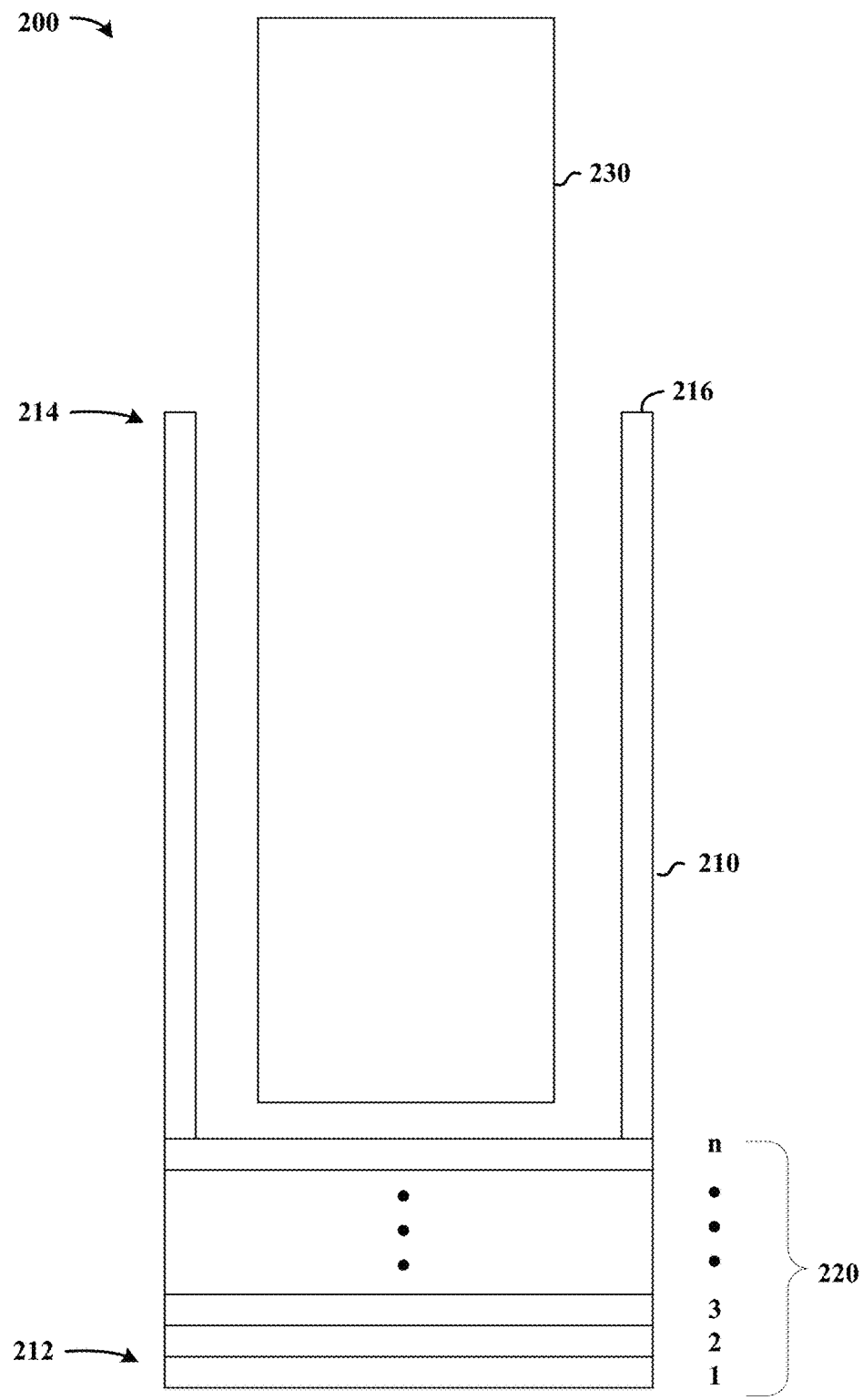
FIG. 2 shows a cross-sectional view of an arrangement for optical imaging, according to another example embodiment of the present invention.

FIG. 2 shows a cross-sectional view of a capillary arrangement 200, according to another example embodiment of the present invention. The capillary arrangement 200 may, for example, be implemented in connection with the capillary 120 in FIG. 1. The capillary arrangement 200 includes a capillary 210, or guiding tube, having a lower closed end 212 and an upper open end 214, with a sidewall 216. Optionally, one or more optical elements 220 (e.g., a lens-type arrangement that focuses or simply passes light, numbered 1-n by way of example) are included near the closed end 212 of the capillary 210. Here, the capillary 210 is shown in a generally cylindrical shape; however, the shape and corresponding arrangement of the side wall 216 can be implemented with a variety of shapes for different applications.

In some applications, the optical elements 220 are implemented with a single glass optical element, which is an optical flat of about uniform thickness. The thickness of this single glass optical element is selected to meet particular applications using considerations such as those related to the desire to prevent fracture or damage to the flat and/or to the desire to reduce the optical distance between the analyzed tissue and an optical probe inserted into the capillary. In one particular application, a glass optical element having a thickness of between about 50 and 500 microns is used to facilitate the aforesaid considerations.

The capillary 210 is adapted for implantation in a sample, such as a tissue sample and/or a live being, with the upper open end 214 extending to an accessible location (i.e., outside and/or at a surface of the sample or live being). After implantation, an optical probe 230 such as an endoscope can be inserted into the exposed upper open end 214 of the capillary 210 for passing light via the closed end 212 to the sample in which the capillary 210 is implanted.

The closed end 212 of the capillary 210 generally facilitates the passage of light, and may include one or more of a polished end, glued end, plastic end, ceramic end, glass end and others. In some applications, the closed end 212 includes one or more passageways that are selectively implemented for the passage of fluids to and/or from a specimen in which the capillary 210 is implanted. In some embodiments, the fluid lines are permanently implanted in a specimen along with the capillary, and in other embodiments, the fluid lines are inserted into the specimen (and reinserted as appropriate for subsequent analysis) via specific routes in the capillary.

In one application, the capillary 210 has a generally cylindrical shape, with inner and outer diameters (as defined by the sidewall 216) respectively about 1.4 mm and 1.6 mm. A generally round light-passing piece is glued at the lower end 212 of the capillary 210 and the arrangement is cured. A fiber grinder is used to polish the capillary, in particular the light-passing piece and the glued lower end 212 of the capillary 210.

In some implementations, the capillary is adapted for implantation into a live being to facilitate optical analysis over the course of time, with the capillary left implanted in the being during times in-between instances of optical analysis. For example, where tissue in a live being is to be studied, the capillary is implanted in the being such that the closed end thereof facilitates the passage of light to and from target areas of the tissue. With this approach, the upper open end 214 of the capillary 210 is available for the insertion of a probe thereto, facilitating access into the live being with the probe from a relative external position. In some instances, the open end 214 of the capillary 210 may be accessible via outer tissue of the being, such as via the skin or skull tissue of the being. In other instances, the open end 214 of the capillary 210 is inside of the live being, but accessible by a probe (e.g., where the capillary is implanted in a region accessible via a blood vessel or via non-invasive or invasive type approaches).

Once implanted, the capillary 210 is used to selectively optically access tissue near the capillary over the course of hours, days, weeks, months or more. In this regard, the study of a live being over time is facilitated, such as for the reaction of the live being to a particular treatment. For example, drugs can be administered to the live being under analysis and the response thereto is readily detected, over time, via the capillary.

In certain applications, additional functional components such as fluid lines, electrodes and others are implemented with the capillary 210. These components may be implemented, for example, to stimulate or otherwise affect the tissue adjacent to the capillary 210, such as by electrically stimulating the tissue or by supplying drugs, dyes or other fluids to the tissue. These components can also be used to monitor the tissue, such as by facilitating electrophysiological recordings or fluidic sampling of specimens to be analyzed using genetic, biochemical, cytometric or other approaches.

The one or more optical elements 220 include one or more of a variety of light-passing arrangements. In one implementation, the one or more optical elements 220 include gradient refractive index (GRIN) optics such as a GRIN lens or GRIN lens array that facilitates the collimation of light. In another application, the optical elements 220 include a variable focal length lens, adaptable for focusing upon subjects at different focal depths. In other applications, the optical elements include a liquid lens.

Figure 3:
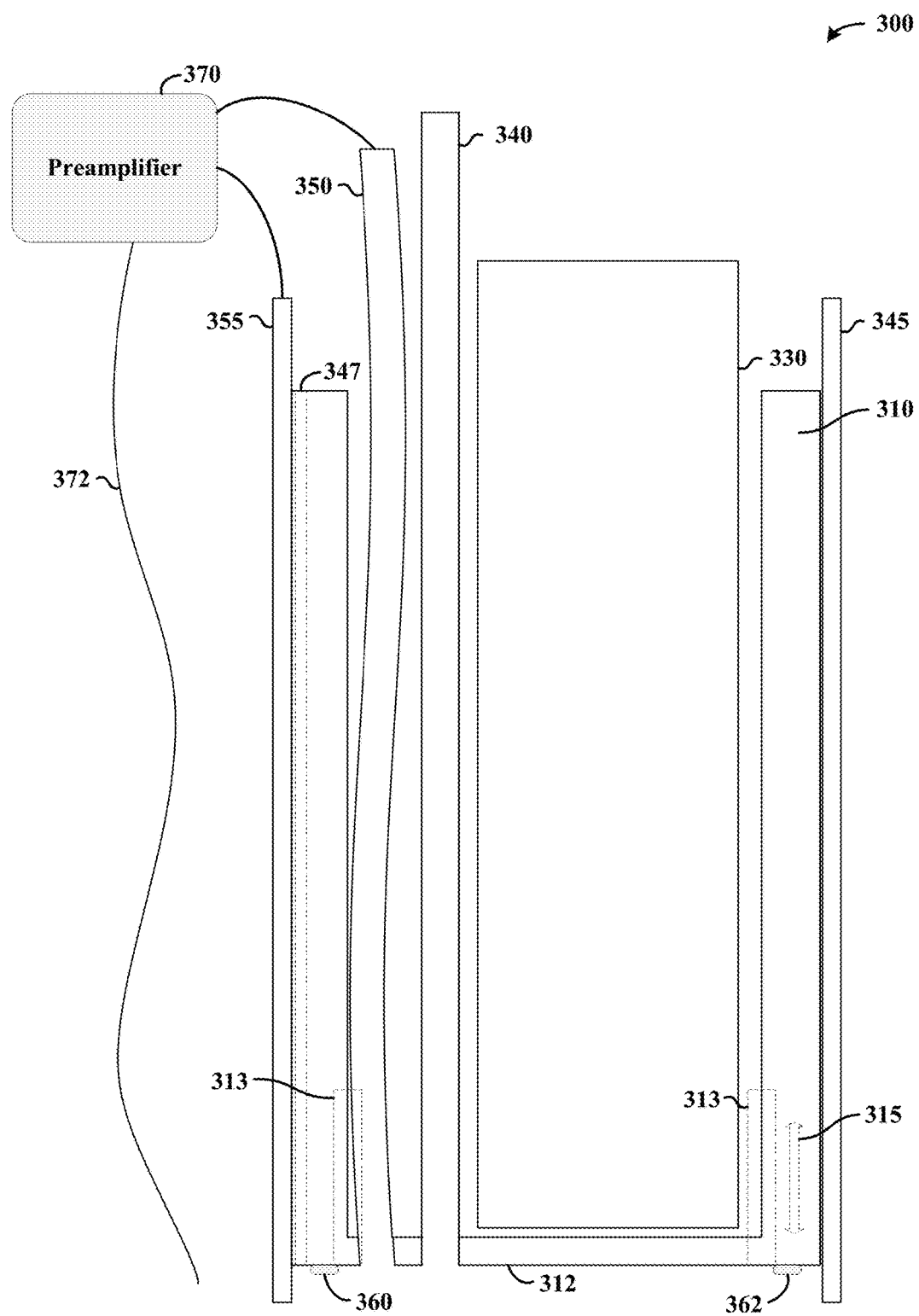
FIG. 3 shows a cross-sectional view of a capillary-type arrangement for analyzing a sample, according to another example embodiment of the present invention.

FIG. 3 is a capillary-type arrangement 300 that selectively facilitates electrical and/or fluidic interaction with a sample, in connection with another example embodiment of the present invention. The electrical and/or fluidic interaction may, for example, involve providing stimulus to the sample, detecting an electrical characteristic of the sample or retrieving fluid from the sample. The arrangement 300 includes a capillary 310, similar to the capillary 210 shown in FIG. 2, with a lower end 312 adapted for implanting into a sample and the passage of light into and out of the sample. As with the capillary 210, the capillary 310 facilitates the use of a light director 330 such as a fiber optic device for delivery of light into the sample and/or passage of light from the sample to an external light detector. In this regard, the lower end 312 includes a lens or other arrangement that facilitates the passage of light and may, for example, include multiple lenses or other arrangements that enhance or otherwise effect the passage of light. In certain applications involving one or more lenses, a MEMS actuator 313 (shown by dashed lines) is coupled to a lens at the lower end 312 and adapted to move the lens as shown by directional arrows 315 to focus upon selected targets.

In another example embodiment, the arrangement 300 further includes a fluidic exchange 340 that facilitates the introduction and/or withdrawal of fluids to/from a sample in which the lower end 312 is embedded. Drugs, stimulating fluids, cleaning fluids or other fluids that facilitate a particular type of analysis of a specimen can be passed into the sample. This fluid supply may facilitate an optical response from the sample, which can be detected via the light director 330. In certain applications, two or more fluid exchange arrangement are thus implemented (e.g., with one for fluid supply and another for fluid withdrawal).

In some applications, the fluid exchange 340 draws fluid from a sample to enhance optical analysis approaches, such as by removing particles or other objects/fluid that may hinder optical analysis via the capillary 310. This fluid may include cells imaged or at a target region to which the arrangement 300 is directed, and in some applications includes other cells from adjacent areas. Moreover, this fluid withdrawal is facilitated over time, during optical analysis, without necessarily re-accessing the sample (i.e., access to the arrangement 300, implanted for a period of time, is facilitated via the capillary 310).

In various embodiments, off-line analysis approaches involve fluid sampling to facilitate one or more of genetic testing using gene chips, biochemical analyses such as microdialysis, and cytometric analyses such as flow cytometry. In some applications, gene chips are implemented for genetic analysis using small sample volumes at the imaging field (i.e., below the capillary 310 at an implanted specimen). Certain applications involve RNA/DNA analysis, which may also involve the use of gene chips. In other applications, a flow cytometry approach involving cellular analysis to classify blood cells is implemented with basic immunology and virology analysis approaches and is selectively implemented with cellular fluorescence methods. In some implementations involving flow cytometry, green fluorescent protein (GFP)-expressing cells are used to reveal protein concentrations and/or protein-protein interactions using fluorescence resonance energy transfer (FRET). In various other applications, cells or molecules within cells to be analyzed are labeled using a variety of techniques so that they emit fluorescence; these techniques may include, for example, antibody labeling, genetic expression of a fluorophore-linked protein and others. In addition to the above, various fluorescent-based analysis approaches are implemented using sampled fluid with post-sampling fluorescent labeling.

Other applications involve biochemical assays such as those involving microdialysis (a biochemical analysis approach) to analyze fluids for small metabolites in conjunction with micro-imaging of a sample via the capillary 310. In some applications, the microdialysis approach implements small hypodermic cannulae attached to the capillary 310 for access to a sample or specimen in which the lower end 312 is embedded. One microdialysis approach involving the capillary 310 is directed to the examination of aggregate neurotransmitter levels in a live rodent brain. Other microdialysis approaches are directed towards characterizing ischemia and head injury, and/or cardiac or pepatic damage or disease.

In one example embodiment, a fluid exchange 345 is implemented with fine (e.g., 31-35 gauge) hypodermic tubing, such as stainless steel tubing, that runs along the side of the capillary 310, for insertion into a sample. This fluid exchange may, for example, be implemented with, or instead of, the fluid exchange 340. In some applications, the fluid exchange 345 is integrated with the capillary 310, as shown by dashed lines 347.

In another example embodiment, the arrangement 300 includes an electrical exchange 350 that is adapted to provide an electrical stimulus to a sample and/or detect an electrical characteristic of a sample in which the lower end 312 of the arrangement 300 is embedded. In some applications, the arrangement 300 includes one or more electrodes near the lower end 312 (e.g., near a portion of the exchange 350 adjacent the lower end 312). When an electrical stimulus is to be applied to the sample, combined electrophysiological and micro-optical measurements are facilitated, with the electrodes implemented to facilitate the application of the stimulus. Similarly, where an electrical response is to be detected, the electrodes are implemented to detect such a response.

In some applications, the electrical exchange 350 is implemented to detect an electrical response of a sample in which the arrangement 300 is embedded. For example, electrodes 360 and 362 near the lower end 312 may be implemented to detect an electrical response to an optical stimulus applied via the light director 330. This electrical response is passed to an external detection arrangement, such as a computer or other processing device, which processes the response and generates a signal or other output that is useful for analyzing characteristics of the sample. For example, images or other characteristics of the sample can be used to analyze the sample or, where used in living samples, to guide surgical procedures.

Certain applications involving the detection of an electrical response from a sample having electrically excitable tissues, aggregate activity in cell populations is observed via measurement of electrical field potentials at electrodes 360 and 362 near the lower end 312 of the capillary 310. Electrocardiogram (ECG), electromyogram (EMG), and electroencephalogram (EEG) analyses are selectively implemented with such applications, using electrical characteristics detected from the sample.

In one implementation, the arrangement 300 includes an electrical probe having electrodes (e.g., tungsten) inserted through a hypodermic tube, fixed to the side or extending through a lower portion of the capillary 310, such as with the electrical exchange 350 or with an external tube 355. This probe is implemented to apply an electrical stimulus, and/or to facilitate the detection of an electrical characteristic from a sample in which the capillary 310 is embedded. In one implementation, the probe includes two or more electrodes in a differential arrangement that facilitates field recordings of aggregate neural activity via voltage changes (e.g., in the range of about 10 μV-2 mV), with common mode fluctuations mutually cancelled.

The arrangement of the electrodes is selected to facilitate the particular application, select stimulus approaches or select response approaches. In one application, the electrodes are insulated with a measurement end exposed and having a metal tip (e.g., of about 5 μm in radius). The tips of the electrodes are arranged between about 100-500 μm below the lower end 312 of the capillary 310 (e.g., via the electrical exchange 350 or the external tube 355 extending below as shown). In certain applications, the electrode tips are curved inwards towards the capillary 310, such that the tip resides near to but outside the field of view of the light director 330.

A differential preamplifier 370 is selectively positioned near the arrangement 300 and adapted to receive signals from electrodes as discussed above. The preamplifier 370 includes a ground wire 372 that can be inserted into a sample animal near to a target below the capillary arrangement 300. Signals from the preamplifier 370 are provided to an amplifier and, in turn, to a computer for digitization, with electrical and image data acquisition synchronized at the computer. This approach may be implemented using, for example, the processor 132 in FIG. 1 or an arrangement as shown in FIG. 4 and discussed further below.

In some electrical detection applications, electrophysiological recordings are used to study small animal models of disease. For instance, an EMG approach provides signatures of muscle contraction, with various applications directed to the examination of disuse atrophy in rats and the examination of mouse models for human cardiac arrhythmias. An EEG approach is implemented for measuring aggregate neuronal activities in the brain, and is selectively used to examine mouse models for sleep deprivation and seizures. Electrical signals are used as a diagnostic for bodily functions that might be fruitfully studied at the cellular level with fluorescence micro-imaging. In one particular application, epilepsy is analyzed using an EEG approach, with aberrant patterns of $Ca^{2+}$ dynamics in epileptic neurons studied in vivo (via the capillary 310) with combined electrical measurements and micro-imaging.

Figure 4:
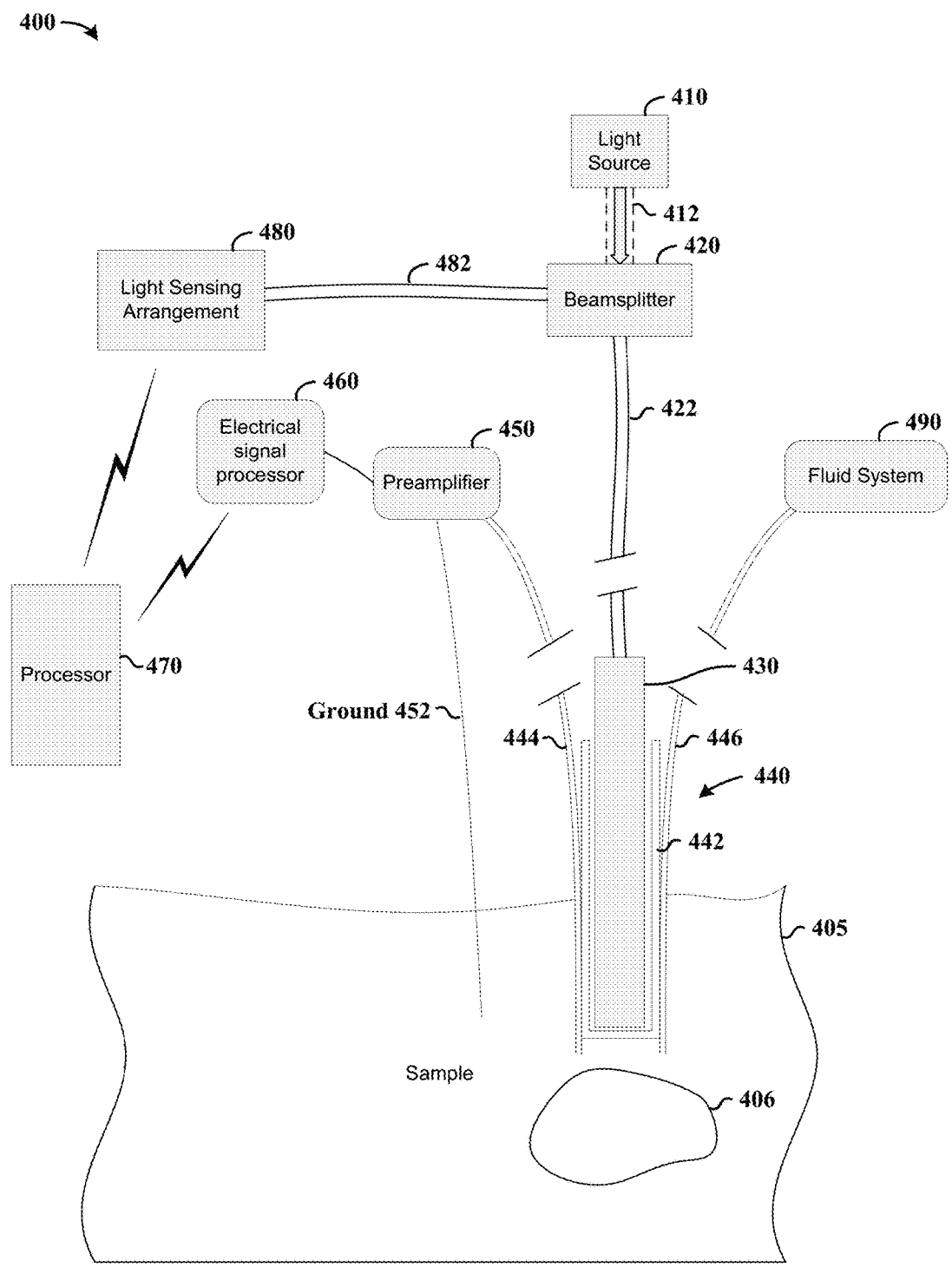
FIG. 4 shows a system for optical imaging with fluid and electrical capabilities, according to another example embodiment of the present invention.

FIG. 4 shows an arrangement 400 for analyzing samples, according to another example embodiment of the present invention. The arrangement 400 includes a capillary arrangement 440 implemented, for example, in a manner commensurate with that discussed in connection with the capillary arrangement shown in FIG. 3. The capillary arrangement 440 includes a capillary tube 442 that is adapted for implantation into a sample 405 for analyzing a target region 406 in the sample over time, and accepts an optical probe 430 that can be inserted from outside the sample to analyze the target region.

The optical probe 430 is coupled to receive light from a light source 410 via a beam splitter 420 and light-passing arrangements 412 and 422, and passes the received light to the target region 406 in the sample 405, via a lower portion of the capillary tube 442. Where appropriate, the lower portion of the capillary tube 442 includes one or more lenses or other light-passing arrangements as described, for example, in connection with FIG. 2. Light from the sample 405 is passed via the capillary tube 442 into the optical probe 430, and via the light-passing arrangement 422 to the beam splitter 420, which directs the sample light to a light sensing arrangement 480 via a light-passing arrangement 482. The light sensing arrangement receives the light, generates a signal in response thereto and passes the signal to a processor 470 for analyzing the light.

An electrical probe line 444 is coupled to the capillary tube 442 and adapted for insertion into the sample 405. Depending upon the particular application, the electrical probe line 444 is selectively implemented with a hypodermic type of tube with a material such as that described above in connection with FIG. 3. The electrical probe line 444 is adapted to receive one or more electrodes, which are inserted into the sample via the probe line and pass an electrical signal to a preamplifier 450, which is further coupled to the sample via a ground 452. The preamplifier 450 amplifies a signal representing an electrical characteristic of the sample detected via the probe in the probe line 444 and passes the amplified signal to an electrical signal processor 460, which processes the signal and passes an output to the processor 470 for analysis. In certain applications, additional electrical probe lines are implemented with the arrangement 400. Furthermore, certain applications involve the use of the electrical probe line 444 and/or additional electrical probe lines to provide an electrical stimulus to the sample 405.

A fluid probe line 446 is adapted to pass fluid between a fluid system 490 and the sample 405. In this manner, fluid is provided to and/or drawn from the sample 405 near the target region 406. In certain applications additional fluid probe lines are implemented with the arrangement 400. Furthermore, in some applications involving multiple fluid probe lines, one or more fluid lines are dedicated for supply or withdrawal of fluid.

Figure 5:
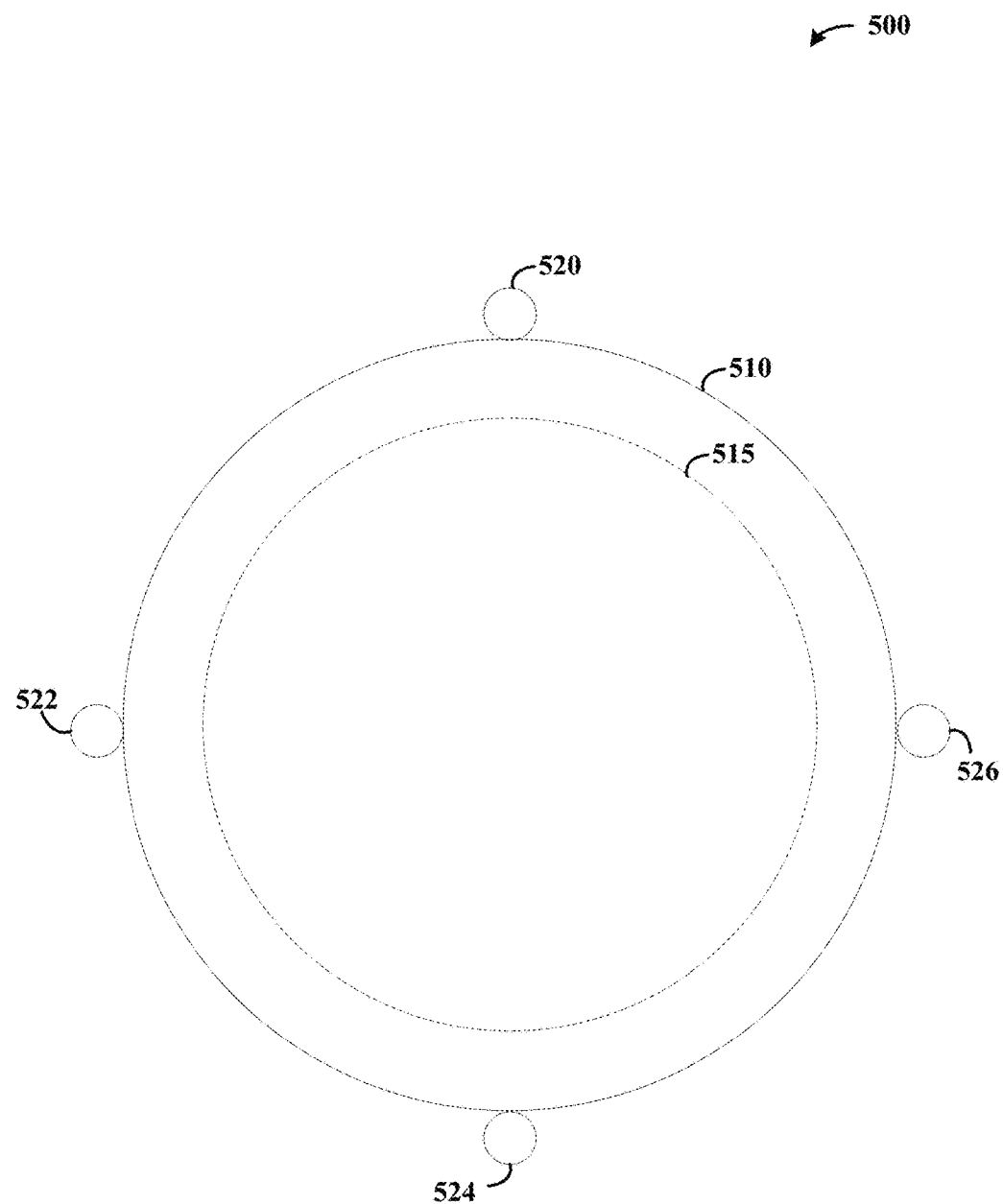
FIG. 5 shows an end view of a capillary arrangement such as that implemented in connection with FIG. 4, according to another example embodiment of the present invention.

FIG. 5 shows a bottom view of a capillary arrangement 500, according to another example embodiment of the present invention. The arrangement 500 may, for example, be implemented in connection with the capillary arrangement 440 in FIG. 4. The arrangement 500 includes a capillary tube with outer and inner walls 510 and 515. Four hypodermic tubes 520-526 are coupled to the capillary tube outer wall 510, and selectively implemented for fluid and/or electrical applications. In other applications, one or more of the hypodermic tubes 520-526 is adapted to receive a fiber optic cable for passing light into a sample (e.g., for oblique illumination).

The approaches discussed above in general and in connection with the example figures are amenable to a variety of applications and further with selected approaches involving various devices, tools or other testing-type apparatus. In this regard, the following approaches are selectively implemented with one or more of the above examples, in connection with various example embodiments.

In one example embodiment, a lens implemented with a capillary-type analysis approach includes a correction lens that cancels optical aberrations. The lens is implemented in a manner similar to that shown, for example, with the optical elements 220 near the lower end 212 of the capillary 210 shown in FIG. 2. This approach facilitates near diffraction-limited resolution for in vivo imaging of fine biological structures discernible with visible light, such as neuronal dendritic spines, mitochondria and stereocilia.

In one embodiment directed to a GRIN lens approach, chromatic and wavefront aberrations present in GRIN micro-lenses are characterized and used to identify a corrective approach which is implemented with lenses used in obtaining an image from the sample. The wavelength dependence of the refractive index profile is numerically modeled, and initial measurements are made to ascertain variation of the on-axis index with wavelength. This approach facilitates modeling of the variation of the focal length of a GRIN objective lens over the visible spectrum. Custom correction lenses are then fabricated with the opposite chromatic dispersion tendencies of GRIN lenses, and facilitate the correction of chromatic and wavefront aberrations. Further, when selectively implemented with achromatic doublet lenses, the correction lenses facilitate the correction of spherical aberrations and coma to first order. Other applications involve triplet lenses. Calculations of spherical aberrations and coma take into account the aqueous environment and the working distance of the GRIN objective lens. These corrective lenses are implemented, for example, with the optical elements 220 in FIG. 2 (alone or with another lens arrangement), facilitating correction with the optical probe 230 where GRIN lenses are implemented.

In one example embodiment, correction lenses are implemented in a doublet arrangement with a crown glass convex lens of relatively low refractive index and dispersion combined with a flint glass concave lens of relatively higher index and dispersion. If $f_1$, $f_2$ and $V_1$, $V_2$ are the respective lens focal lengths and Abbe numbers (a measure of chromatic dispersion), then the Abbe condition for having the same focal length at the top and bottom of the spectral range is $f_1V_1+f_2V_2=0$. This approach can be facilitated by a doublet that has a plano-convex shape, and which thus suffers minimally from spherical aberration and coma. The Abbe condition of the doublet arrangement is modified so $f_1V_1+f_2V_2$ is not zero, balancing the chromatic aberrations from our GRIN micro-lenses. In some applications, this modification of the Abbe condition is facilitated via choice of lens materials, rather than alteration of the doublet's shape, inhibiting spherical aberrations. In some applications, separate correction lenses are implemented for one- and two-photon imaging approaches, since the relevant spectral ranges for the different approaches are quite distinct. In one implementation, a relay correction lens is combined with an objective correction lens to facilitate correction.

One example imaging technique that may be used in connection with one or more example embodiments discussed herein involves laser scanning fluorescence microscopy. In laser scanning fluorescence microscopy, focused laser light is scanned across a sample. Fluorescent probes inside of the sample absorb the laser light and emit fluorescence at a different wavelength. The fluorescence light is collected and used to visualize the sample. In some applications, this approach is implemented to facilitate sectioning; that is, the sample may be visualized sub-surface and at varying depth profiles, with stimulation and response light passed via a lens at an embedded end of a capillary. In addition, fluorescent probes may be attached to a structure of interest inside of a biological sample such as a protein, a drug, a sequence of DNA, an RNA sequence or a selected molecule. Laser scanning fluorescence microscopy then allows for visualization of the distribution of said structure of interest.

In some applications, laser scanning fluorescence microscopy is combined with a nonlinear optical process such as two-photon absorption, typically referred to as two-photon fluorescence microscopy or two-photon laser-scanning fluorescence microscopy. With this two-photon microscopy approach, a fluorescent probe inside of the sample (i.e., at a location below the implanted end of a capillary) absorbs two-photons from a laser pulse that uses short pulses or pulses in the femtosecond to picosecond range and emits a fluorescence photon at a lower wavelength. This approach is generally beneficial in reducing photobleaching and phototoxicity, relative to other conventional approaches, and is generally robust to light-scattering inside of the sample.

Other nonlinear optical processes used in connection with various examples visualize surface and sub-surface structures inside of a sample via laser-scanning of a sample with one or multiple lasers (i.e., as directed by a MEMS mirror) via a capillary-type device. In one instance, a harmonic generation approach such as second-harmonic generation (SHG) or third harmonic generation (THG) is used to generate a nonlinear response that is detected and used to garner information about a sample. In other instances, nonlinear processes such as Raman scattering or Raman spectroscopy, or Coherent Anti-Stokes Raman Scattering (CARS) are used in stimulating and analyzing sample.

In the above and other example embodiments of the present invention, various characteristics of light direction approaches (such as those involving a MEMS mirror implementation and/or associated optical arrangements) are directed to specific functions relating to the stimulation of and/or detection of nonlinear optical characteristics in a sample. In this regard, certain characteristics of the above approaches and those shown, for example, in FIGS. 1-4 are selectively tailored for nonlinear type conditions, as discussed further below and otherwise.

In various example embodiments, a nonlinear optical detection system such as that discussed above further includes implantable stimulation-facilitating devices. One application involves the use of a system including a light source, MEMS mirror, fluorescence probes (for implantation with a sample) and a wavelength-dependent light collection apparatus. The fluorescence probes are configured to interact with light from the source, directed by the MEMS mirror via a lower end of a capillary, and to facilitate a nonlinear response of the sample in which the probes are implanted. This response includes light that is passed to the detector via the capillary and is generally characterized in that the wavelength of the light is different than the wavelength of the source light. Other nonlinear optical detection applications involve the use of devices separate from or in addition to the fluorescence probes, with such devices similarly facilitating the generation of a detectable nonlinear optical response of the sample. These other applications may include, for example, harmonic generation applications, Raman scattering applications or Coherent Anti-Stokes Raman Spectroscopy (CARS) applications, e.g., as discussed above.

For general information regarding optical analysis and for specific information regarding approaches to analysis that may be implemented in connection with one or more example embodiments herein, reference may be made to the following patent documents: U.S. Pat. Nos. 6,485,413 and 6,423,956, and U.S. Patent Application Publication Number US 2003/0142934; each of these is fully incorporated herein by reference. For example, the mirrors implemented in one or more of these example patent documents may be implemented in connection with various example embodiments discussed herein. One or more different types of light sources are implemented, depending upon the application and availability. In some applications, more than one light direction and/or collection arrangement is used to provide additional functionality.

While the present invention has been described with reference to several particular example embodiments, those skilled in the art will recognize that many changes, including those discussed in the preceding paragraph, may be made thereto without departing from the spirit and scope of the present invention.

What is claimed is:

1. A method of repeatedly generating in vivo, cellular resolution images from a target region in a subject in iterative imaging sessions, comprising:
    providing an imaging system, the imaging system including (a) a light conduit, (b) a housing (1) affixed to the subject and (2) configured and arranged to repeatedly accept, and provide stable optical access to the target region for the light conduit, and (c) a detector configured to (1) generate a signal from light collected by the light conduit, and (2) pass said signal to an image processor used to generate structural cellular resolution images;
    enabling the optical access, with the aid of the imaging system, into the target region for a time period lasting from a first iterative imaging session to a subsequent iterative imaging session; and
    conducting iterative cellular resolution imaging sessions with the aid of the imaging system, each imaging session including
        (i) directing light to the target region with aid of the light conduit, thereby inducing response light from the target region, and
        (ii) generating structural cellular resolution in vivo images from the response light with the aid of the light conduit and the detector,
    wherein the step of conducting iterative cellular resolution imaging sessions comprises (1) removing the light conduit from the housing after the first iterative imaging session, (2) re-inserting the light conduit into the housing to perform the subsequent imaging session, and (3) keeping the housing affixed to the subject between the first iterative imaging session and the subsequent imaging session.

2. The method of claim 1, wherein the light conduit comprises one or more of a single conduit, two or more light conduits, a fiber optic conduit, a microendoscope probe, or a bundle of optical fibers.

3. The method of claim 1, further comprising allowing the subject to engage in freely ranging behavior after removing the light conduit from the housing after the first iterative session and before the subsequent imaging session.

4. The method of claim 3, wherein the subject engages in the free ranging behavior during a time period between the first iterative imaging session and the subsequent imaging session, during which light conduit is removed from the housing.

5. The method of claim 1, wherein the step of conducting iterative cellular resolution imaging sessions further comprises focusing light to a selected depth to access the target region within a tissue sample.

6. The method of claim 1, wherein the imaging system comprises one or more optical elements configured to pass light between the target region and the detector.

7. The method of claim 6, wherein the one or more optical elements comprise a beamsplitter.

8. The method of claim 1, further comprising resolving, during the cellular imaging session, structures with a dimension of dendritic spines, stereocilia, or mitochondria.

9. The method of claim 1, wherein the target region comprises a subcutaneous tissue sample.

10. The method of claim 1, wherein a time period between the first iterative imaging session and the subsequent imaging session during which the light conduit is removed from the housing is 24 hours or more.

11. The method of claim 1, wherein the subject is a live rodent.

12. The method of claim 11, wherein the target region is a brain of the live rodent.

13. The method of claim 1, further comprising monitoring electrophysiological responses of the target region in vivo.

14. The method of claim 1, wherein the image processor is a computer configured to reconstruct and display the cellular resolution images.

15. The method of claim 1, wherein the light collected by the light conduit is a response light from the target region.

16. The method of claim 15, wherein the light from the light sources passes through a beamsplitter before being collected by the light conduit.

* * * * *